(12) United States Patent
Chenite et al.

(10) Patent No.: US 7,098,194 B2
(45) Date of Patent: Aug. 29, 2006

(54) COMPOSITION AND METHOD TO HOMOGENEOUSLY MODIFY OR CROSS-LINK CHITOSAN UNDER NEUTRAL CONDITIONS

(75) Inventors: Abdellatif Chenite, Kirkland (CA); Mohammed Berrada, Montreal (CA); Cyril Chaput, Montreal (CA); Fouad Dabbarh, Montreal (CA); Amine Selmani, Laval (CA)

(73) Assignee: Biosyntech Canada, Inc., Laval (CA)

( * ) Notice: Subject to any disclaimer, the term of this patent is extended or adjusted under 35 U.S.C. 154(b) by 325 days.

(21) Appl. No.: 10/298,257

(22) Filed: Nov. 15, 2002

(65) Prior Publication Data

US 2003/0129730 A1 Jul. 10, 2003

Related U.S. Application Data

(60) Provisional application No. 60/331,415, filed on Nov. 15, 2001.

(51) Int. Cl.
*A61K 31/722* (2006.01)
*C08B 37/08* (2006.01)

(52) U.S. Cl. .............................. 514/55; 514/54; 536/20; 536/18.7; 536/124

(58) Field of Classification Search ................... 514/55, 514/54; 536/20, 18.7, 124
See application file for complete search history.

(56) References Cited

U.S. PATENT DOCUMENTS 4,424,346 A     1/1984  Hall et al.
4,605,623 A  *  8/1986  Malette et al. .............. 435/377
4,996,307 A     2/1991  Itoi et al.
5,977,330 A    11/1999  Lohmann et al.

OTHER PUBLICATIONS

Shimizu et al. (Nippon Kagaku Kaishi (1998), (9), 637–641) (Abstract Sent).*

Hirano et al., *Biopolymers*, 15, 1685, 1976, Kubota et al., *Polymer Journal*; 29, 123, 1997.

* cited by examiner

*Primary Examiner*—Elvis Q. Price
*Assistant Examiner*—Michael C. Henry
(74) *Attorney, Agent, or Firm*—Nixon Peabody LLP

(57) ABSTRACT

In accordance with the present invention there is provided a new composition and method for chemically modifying chitosan, including N-substituting or N-cross-linking, under homogeneous conditions by providing neutral aqueous chitosan solutions with enhanced reactivity. The method comprises the steps of i) preparing a clear aqueous solution of chitosan, said solution comprising 0.1 to 10% by weight of a chitosan, and 0.1 to 20% by weight of at least one buffering agent having a pKa between 6.0 and 7.6, said solution having a pH ranging from 6.8 to 7.2; and ii) dissolving homogeneously at least one reagent into the solution of step a), said reagent being reactive toward amine groups of chitosan; and said reagent being at a concentration from 0.01 to 10% by weight. The chitosan in the aqueous solution is chemically modified or cross-linked by a selective substitution on the amino group of chitosan.

23 Claims, 7 Drawing Sheets

COMPOSITION AND METHOD TO HOMOGENEOUSLY MODIFY OR CROSS-LINK CHITOSAN UNDER NEUTRAL CONDITIONS

CROSS-REFERENCE TO RELATED APPLICATIONS

This application claims the benefit of U.S. Provisional Application No. 60/331,415, filed Nov. 15, 2001 under 35 U.S.C. § 119(e).

TECHNICAL FIELD

The present invention relates to a method for chemically modifying chitosan, including N-substituting or N-cross-linking, under homogeneous conditions by providing neutral aqueous chitosan solutions with enhanced reactivity.

BACKGROUND OF THE INVENTION

Chitosan is an amino-polysaccharide obtained by alkaline deacetylation of chitin, a natural polysaccharide found in the exoskeletons of shellfish and insects. Chitin cannot be dissolved in water except in concentrated mineral acid aqueous solutions, during which dissolution there is a decrease in the degree of polymerization and probably removal of some acetyl groups. Such characteristics have undoubtedly limited its investigation and utilisation in many fields, in spite of the advantages claimed for chitin and its great abundance in nature. In contrast, the numerous industrial applications claimed for chitosan, are in part attributed to its good solubility in mild acidic media, via the formation of ammonium groups.

Conventionally, chitosan is dissolved in aqueous acidic media and can be maintained in solution up to a pH near 6.2 (just below its pKa of ~6.3). Under these conditions, the reactivity of chitosan is significantly decreased, because of the predominance of non-reactive $NH_3^+$ groups compared to $NH_2$ groups, and the latter are known as nucleophilic and therefore susceptible to react with various electrophiles due to their unshared pair of electrons. Nonetheless, a variety of chemical approaches have been employed to homogeneously modify chitosan under acidic conditions (pH<6), specifically by reacting aldehydes, acid chlorides, acid anhydrides and epoxides, and the like, with chitosan's amino groups.

To achieve chitosan modification under homogeneous conditions, prior art reports the addition of an organic co-solvent (methanol, pyridine, etc.) to the acidic chitosan solution, in order to enhance the chitosan reactivity (U.S. Pat. Nos. 4,996,307 and 4,424,346) or the use of a large excess of reagent (Hirano et al., *Biopolymers*, 15, 1685, 1976, Kubota et al., *Polymer Journal*, 29, 123, 1997). However, the presence of an organic co-solvent or an excess of reagent is not desired for medical applications. In addition environmental concerns are providing strong incentive for eliminating organic solvent and reducing the use of reactive reagents. Furthermore, at low pH (below 6.2) the number of free amino groups is insufficient to allow the chitosan to undergo a reaction with some electrophilic reagents, particularly those bearing benzoimidate or epoxy groups.

All studies concerned with the N-substitution of chitosan confirm the importance of availability and activation of chitosan's free, non-ionized, amino groups. A recent patent (U.S. Pat. No. 5,977,330) claims the N-substitution of chitosan with good yield via a high activation of chitosan's free amino groups by controlling two factors which enhance the chitosan reactivity, namely, the neutral pH and the use of an organic solvent. However, in addition to an organic solvent, the reaction was heterogeneously performed on re-precipitated chitosan due to the impossibility of maintaining chitosan in solution under neutral pH conditions, when conventional alkali solutions such as NaOH or $NH_4OH$ are used as neutralising agents.

It would be highly desirable to be provided with an alternative method to homogeneously modify or cross-link chitosan, by providing an aqueous chitosan solution, which can be maintained quite in solution in the vicinity of neutral pH, since under such conditions the number and the reactivity of free amino groups are considerably enhanced.

It would also be highly desirable to be provided with an alternative method that would allow the elimination of organic solvent and prevent the use of an excess of reagent, and would nonetheless still render possible reactions between chitosan and electrophilic functional groups, which usually require neutral pH to occur.

SUMMARY OF THE INVENTION

One aim of the present invention is to provide a new method for the chemical modification, including the N-substitution or the N-cross-linking of chitosan, under homogeneous conditions by providing neutral aqueous chitosan solutions with enhanced amino-reactivity.

Another aim of the present invention is to provide a new method for the chemical modification or the N-cross-linking of chitosan, under homogeneous conditions that would prevents the use of organic solvent or a large excess of reactive reagent.

Recently, the inventors found various buffers, which allows the neutralisation of chitosan solution up to neutral or nearly neutral pH without inducing immediate gel-like precipitation. With these buffers, homogeneous reactions involving amino groups of chitosan can be performed under these conditions, without the need for an organic co-solvent (methanol, pyridine etc.) or excess of reagent. Subjecting the neutralised chitosan to any reactions with electrophiles in homogeneous solution, leads to improvements in yield and quality of the end product, that is the modified chitosan.

The method and composition of the present invention thus allow the elimination of organic solvent and organic catalyst, and enables the reduction of reactive reagent, usually involved in chemical modification of chitosan, while improving yield and quality of the end-product, that is modified chitosan.

In accordance with the present invention, there is thus provided a N-modified chitosan composition comprising:
 a) to 10% by weight of chitosan in a clear aqueous solution;
 b) 0.1 to 20% by weight of at least one buffering agent having a pKa between 6.0 and 7.6, and
 c) 0.01 to 10% by weight of at least one reagent reactive toward amine groups of chitosan,
wherein said N-modified chitosan composition has a resulting pH ranging from 6.8 to 7.2.

Still in accordance with the method of the present invention, there is provided a method for chemically-modifying or cross-linking chitosan under homogeneous conditions, said method comprising the steps of:
 a) preparing a clear aqueous solution of chitosan, said solution comprising 0.1 to 10% by weight of a chitosan, and 0.1 to 20% by weight of at least one buffering agent having a pKa between 6.0 and 7.6, said solution having a pH ranging from 6.8 to 7.2; and b) dissolving homogeneously at least one reagent into the solution of step a), said reagent being reactive toward amine groups of chitosan; and said reagent being at a concentration from 0.01 to 10% by weight, wherein said chitosan in the aqueous solution is chemically modified or cross-linked by a selective substitution on the amino group of chitosan.

The method may further comprises if desired a step of purification. Such step of purification may consist of a) dialysing the chemically-modified or cross-linked chitosan; b) precipitating the chitosan obtained in step a), with a basic solution; c) washing the precipitated chitosan of step b); and d) air-drying the washed chitosan of step c).

Further in accordance with the present invention, there is provided a method of preparation of a chitosan based aqueous gel composition which comprises the steps of:
a) preparing a water-based solution component comprising 0.1 to 10% by weight of chitosan, having a degree of deacetylation between 70% and 100%, and 0.1 to 20% by weight of a glycerophosphate salt; said solution having a pH in the range between 6.4 and 7.2;
b) preparing a solid component comprising at least a water-soluble mono-functionalized methoxy-poly (ethylene glycol) reagent, having a molecular weight between 2,000 and 10,000; and
c) mixing homogeneously said solution component and said solid component to form a uniform and homogeneous solution, having 0.01 to 10% by weight of the mono-functionalized methoxy-poly(ethylene glycol) reagent, wherein a homogeneous N-modification or N-grafting of chitosan chains and the formation of a homogeneous uniform aqueous gel occurs.

For the purpose of the present invention the following terms are defined below.

The expression "homogeneous modification of chitosan" refers herein to a chemical substitution on the free amine groups of chitosan, while chitosan are in aqueous solution. The amine groups being reactive $NH_2$ groups and the chemical substitution being also called N-substitution.

The expression "homogeneous acylation of chitosan" refers herein to an N-acylation reaction of the chitosan achieved via the addition of acid anhydride to a nearly neutral aqueous chitosan solution. In one embodiment, the N-acylation reaction is allowed to proceed under continuous stirring at room temperature. The reaction time is generally about 4 to about 24 hours. At the end of the reaction, the N-acylated product is dialysed against pure water, precipitated with basic solution, washed and air dried.

The expression "homogeneous chemical N-cross-linking of chitosan" refers herein to the chemical reaction that is achieved with the addition of bi(di)-functional reactive reagents to the neutral aqueous solution of chitosan, thus resulting in a hydrated three-dimensional chitosan network. The di-functional reagents selected herein to exemplify the present method are glyoxal and polyethylene glycol diglycidyl ether. Cross-linked chitosan solution generally results in a gel. The gel can be dialysed against pure water and isolated in spongy form after freeze-drying. The gel can also be formed around living cells or biologically active materials.

The expression "mono-functionalized" is used herein to qualify a reagent such as a molecule, an oligomer or a polymer having one chemical group, reactive with the free amines.

The expression "di- or bi-functionalized" is used herein to qualify a reagent such as a molecule, an oligomer or a polymer having two chemical groups, each reactive with chitosan's free amines.

The term "gel" is used herein at large and refers to biopolymeric aqueous gels of any kind, including particularly loose gels, hydrogels, etc.

DETAILED DESCRIPTION OF THE PREFERRED EMBODIMENT

Figure 1A:
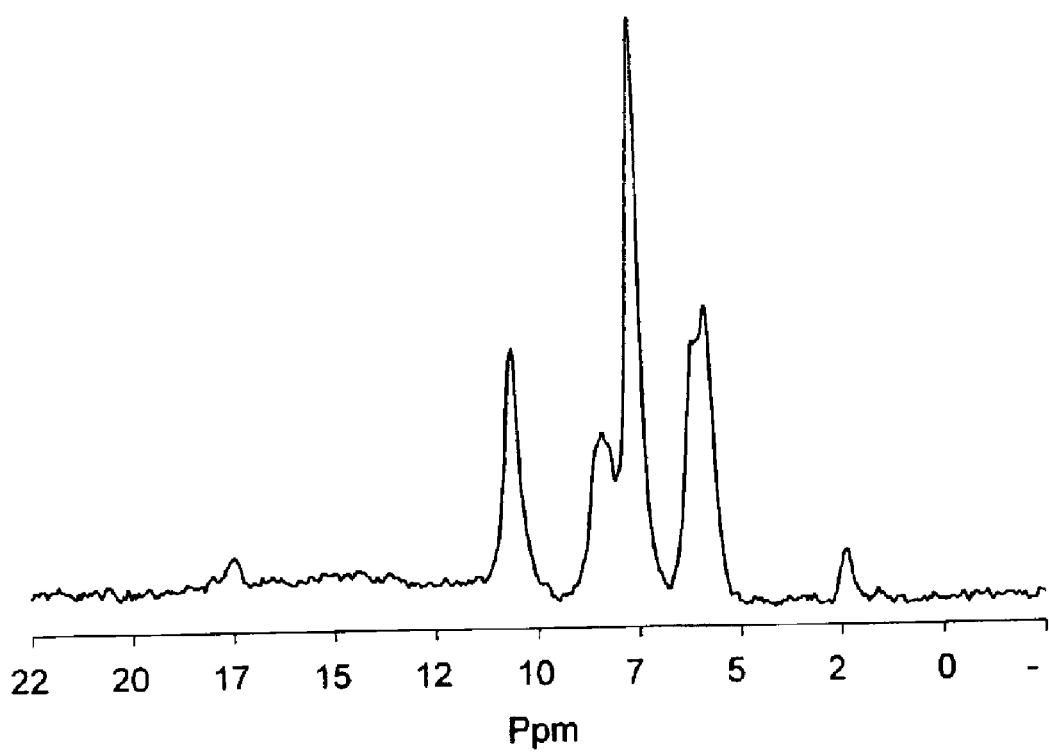
FIG. 1A illustrates a $^{13}C$ NMR spectrum of chitosan with 86% of glucosamine unit.

In accordance with the present invention, there is provided a homogeneous solution of chitosan prepared by dissolving a known quantity of chitosan in an aqueous acidic solution. The pH of the resulting solution is controlled to be maintained near 5.0. In the present method, the starting chitosan preferably has a degree of deacetylation of 70% or higher. The aqueous acid solution of chitosan is neutralised with appropriate buffer, which should increase the pH of the solution to be in the vicinity of 7, without inducing the gel-like precipitation. The appropriate buffer should be chemically inert. It is advisable to select a relatively weak buffering agent with a useful buffering range that encompasses the pH of precipitation of the chitosan solution (pH~6.2). Preferably, the agent has a pKa between 6.0 and 7.6.

According to the present invention, a reactive reagent or a cross-linking agent is thereafter added to the neutralised chitosan solution to allow reaction with free reactive amino groups of chitosan in high yield.

According to the preferred embodiment of the invention, there is provided a chitosan composition that comprises 0.1 to 10% by weight of chitosan in a clear aqueous solution, 0.1 to 20% by weight of at least one buffering agent, said buffering agent being sufficient to rise the pH in the range between 6.4 and 7.2, and 0.01 to 10% by weight of at least one reagent reactive toward amine groups of the chitosan, and wherein chitosan undergoes a homogeneous N-modification, N-grafting or N-cross-linking. In such an embodiment, the starting chitosan has a degree of deacetylation between 70% and 100%, and the buffering agent has a pKa between 6.0 and 7.6.

In the present invention, it is intended that any cationic biopolymer having free amine groups and being soluble in acidic aqueous media, "behaving as chitosan" may be selected.

In a preferred embodiment, the buffering agent of said chitosan composition is a biological buffer. It can be preferentially selected in a group comprising phosphate salts, glycerophosphate salts, N,N-bis[2-hydroxyethyl]-2-aminoethanesulfonate (BES), 3-[N,N-bis(2-hydroxyethyl)amino]-2-hydroxypropanesulfonate (DIPSO), N-[2-hydroxyethyl] piperazine-N'-4-butanesulfonate (HEPBS), N-[2-hydroxyethyl] piperazine-N'-3-propanesulfonate (HEPES), 2-[N-morpholino] ethanesulfonate (MES), 4-[N-morpholino]butanesulfonate (MOBS), 3-[N-morpholino] butanesulfonate (MOPS), 3-[N-morpholino]-2-hydroxypropanesulfonate (MOPSO), bis[2-hydroxyethyl] iminotris-[hydroxymethyl] methane (BIS-TRIS), BIS-TRIS propane, or any derivatives, or any mixtures thereof. The preferred glycerophosphate salts are generally disodium glycerophosphate salts.

In the present invention, it is intended that any water-soluble phosphate, carbonate, sulfate, sulfonate compounds having an appropriate pKa, including salts, and the like, may be used as a biological buffer of the chitosan solution.

In a preferred embodiment, the reagent has at least one reactive group, meaning a chemical group to react with the amine groups of chitosan. It is preferentially selected in a group of chemical reagents comprising aldehydes, anhydride acids, azides, azolides, carboimides, epoxides, esters, glycidyl ethers, halides, imidazoles, imidates, succinimides, succinimidyl esters, acrylates and methacrylates, or any mixtures thereof.

In another preferred embodiment, the reagent is a water-soluble molecule or macromolecule that has at least two pendant reactive groups, wherein such groups are selected in a group comprising aldehydes, azides, azolides, esters, glycidyl ethers, halides, imidazoles, imidates, succinimides, succinimidyl esters, acrylates and methacrylates, or any combinations thereof. The reagent can be preferentially a mono-functionalized water-soluble polymer selected in group comprising poly(alkylene glycol), poly(alkylene oxide), poly(vinyl alcohol) and poly(vinyl pyrrolidone), and the like. This comprises poly(alkylene oxide) derived copolymers with other polymers, such as for example a poly(ethylene oxide)-poly(lactic acid) or a poly(ethylene oxide)-poly(caprolactone) block copolymers, and the like. Such mono-functionalized water-soluble polymers comprise methoxy PEG-succinoyl-N-hydroxysuccinimide ester (mPEG-suc-NHS), methoxy PEG-carboxymethyl-NHS, and the like. The reagent can be preferentially a di-functionalized water-soluble polymer selected in group comprising poly(alkylene glycol), poly(alkylene oxide), poly(vinyl alcohol) and poly(vinyl pyrrolidone), and the like. For example, such reagent can be preferentially selected among poly(ethylene glycol) di-glycidyl ether, poly (ethylene glycol) di-tresylate, poly(ethylene glycol) di-isocyanate, poly(ethylene glycol) di-succinimidyl succinate, poly(ethylene glycol) di-succinimidyl propionate, di-succinimidylester of carboxymethylated poly(ethylene glycol), poly(ethylene glycol) di-benzotriazole carbone, carbonyldiimidazole di-functionalized poly(ethylene glycol), or poly(ethylene glycol) di-nitrophenyl carbonate, and the like.

In another embodiment, the reagent is selected among aldehydes, such as glutaraldehyde, formaldehyde, glyoxal, or a bifunctional propionaldehyde based reactive chemical, or any derivatives thereof.

In another embodiment, the reagent is selected among chemicals that have an ester reactive group, such as bi-succinimidyl, sulfo-succinimidyl, N-hydro-succinimidyl or N-sulfo-succinimidyl ester group, or any derivatives thereof.

The reagent can also be selected among chemicals that have an imidoester reactive group, such as di-methylpimelimidate, di-methyladipimidate, di-methylsuberimidate, or di-methylpropionimidate group, or any derivatives thereof.

The reagent can also be selected among chemicals that have have a phenyl azide, hydrazide, hydroxyphenyl azide or nitrophenyl azide group.

In an embodiment of the present invention, the modification of chitosan is a selective substitution on the amine group, and preferentially a homogeneous N-substitution on chitosan chains.

In another embodiment, the reagent is an acid anhydride such as acetic anhydride, propionic anhydride or butyric anhydride, and the like.

In an embodiment of the present invention, the modification of chitosan is a selective substitution on the amine group, and preferentially a homogeneous N-acylation of chitosan chains.

In an embodiment of the present invention, the modification of chitosan is a selective substitution on the amine group, and preferentially a homogeneous cross-linking of chitosan chains via the amine groups.

Such a modification of chitosan chains can result into the bulk formation of a homogeneous and uniform chitosan gel with a physiological pH. This resulting gel formation may be observed ex vivo such as in vitro as well as in situ or in vivo within the body of mammalians or humans. This resulting gel formation may be used to design self-gelling chitosan-based materials. The gel produced with the method can be a hydrogel, and can be freeze-dried to produce a continuous and uniform chitosan sponge with enhanced mechanical performances.

In other embodiments, the composition can comprise a pharmaceutical agent, a therapeutic agent or a bioactive agent, or any combinations thereof. In a same way, it can also comprise suspended living mammalian (animal or human) cells.

In an embodiment of the invention, the chitosan composition, as previously described, can be used for transporting living cells in vivo, for producing cell/polymer hybrids in vitro, for testing or diagnostic purposes in vitro, or for implantation in vivo in cavities, organs or tissues.

It is intended that the chitosan composition of the present invention can be used for designing, developing and manufacturing secondary materials or products of industrial, medical, surgical, pharmaceutical interest.

In a further embodiment of the present invention, a method is described to chemically-modify or cross-link chitosan under homogeneous conditions. The method comprises the steps of a) preparing a clear aqueous solution of chitosan, said solution comprising water, and 0.1 to 10% by weight of a chitosan, and 0.1 to 20% by weight of at least one buffering agent, said solution having a pH ranging from 6.4 to 7.2, and b) dissolving homogeneously at least one reagent into said solution, said reagent being reactive toward amine groups of chitosan, and said reagent being at a concentration from 0.01 to 10% by weight, wherein the chitosan in aqueous solution is chemically modified by a selective substitution on the amino groups. In such an embodiment, the chitosan has a degree of deacetylation between 70% and 100%, and the buffering agent has a pKa between 6.0 and 7.6.

In one embodiment, an end-activated mPEG is added to a neutral or nearly neutral solution of chitosan (preferably a partially reacetylated chitosan prepared from 100% deacetylated chitosan). Under these conditions, the activated end allows rapid grafting of mPEG on chitosan chains via a covalent bond with the amino groups of chitosan. The resulting mPEG-grafted-chitosan chains in the solution undergo self-association via intermolecular forces such as hydrogen bonding between amino hydrogen from chitosan and oxygen from polyether.

Other monomethoxy polyalkylene oxides or their derivatives such as multi-blocs (example for: monomethoxy poly(ethylene glycol)-poly(lactide) copolymer . . . ) can also be end-activated and grafted onto chitosan under the same conditions. The activated end consists on anhydride function or succinimide ester group, both considered non toxic and suitable for the in-vivo administration.

The molecular weight of the chitosan can vary depending on the desired application. In most instances, the molecular weight is about 10,000 to 5,000,000 mol. wt., and more preferably about 50,000 to 500,000 mol. Wt. When the material is monomethoxy polyethylene glycol, the molecular weight is about 500 to about 20,000 mol. Wt., and more preferably about 2,000 to 10,000 mol. Wt.

Methoxy PEG-succinoyl-N-hydroxysuccinimide ester (mPEG-suc-NHS), and methoxy PEG-carboxymethyl-NHS (mPEG-cm-NHS) have been reacted with chitosan under homogeneous conditions in mild aqueous solution to produce hydrogel formulations. Such modified chitosan based formulations may form gels, at room temperature, within a few minutes depending upon the formulation characteristics.

Prior to the gel formation, the formulation can also be loaded with optional materials, such as proteins, drugs, cells, hemostatic agents, genes, DNA, therapeutic agents, antibiotics, growth factors, inorganic materials and the like.

The composition may be injectable or extrudable prior to said formation of a homogeneous uniform aqueous gel, and may be injected into a mammalian body, animal or human, prior to said formation of a homogeneous uniform aqueous gel. An ideal situation is when the formation of a homogeneous uniform aqueous gel is reached in vivo within the body of a mammalian, animal or human, for therapeutic purposes within a body cavity, an organ or a tissue.

Additional ingredients may be incorporated within the composition, either the solution component or the solid component. These ingredients comprise a solid therapeutic, pharmaceutical or bioactive agent as well as a material of biological origin, such as autograft, allograft xenograft, crushed bone, demineralized bone powder, solid animal or human proteins, animal or human living cells, and the like. Ceramic or inorganic materials, such as bioglass, calcium phosphate, calcium sulfate, calcium carbonate, and the like, may be incorporated as well at various loading levels.

The composition may enter into the preparation of a composite or hybrid material of industrial, pharmaceutical or medical interest, and particularly into the preparation of a surgical material, such an injectable, an implant or a prosthetic device. Of particular interest is when the composition enters into the preparation of a solid composite implant containing calcium and phosphate compounds.

The composition is preferentially applied to surgical material for repairing, restoring, replacing or regenerating animal or human body tissues and/or animal or human body organs.

Application of modified/cross-linked chitosan compositions:

Chitosan compositions where chitosan is homogeneous N-modification, N-grafting or N-cross-linking may be of specific interest specially by their capacity to form rapidly strong aqueous gels.

Such gel-forming chitosan compositions can be incorporated for:

injectable gel-forming formulations for drug, proteins, or cell delivery purposes, etc; Drugs, proteins can be incorporated under a soluble, sparingly soluble or quasi non-soluble form;

gel-strip materials for medical and surgical applications in drug delivery, wound healing, tissue repair, tissue and cell engineering, body's part replacement, etc; Gel-strip materials are preformed at preparation or manufacture;

scaffold for composite construction for ultimately forming a solid composite or hybrid material, incorporating the chitosan-based gel; Such chitosan formulation enters into the formulation of mineral composite hybrid composites; For example, composite self-hardening calcium phosphate compositions ("calcium phosphate cement") can be prepared from a modified chitosan system.

encapsulating, embedding or carrying matrix for: solid organic or inorganic particles such as calcium phosphates, calcium sulfate, calcium carbonate; microparticles such nanospheres, microspheres; solid protein particles such as demineralized bone proteins and the like; solid polymeric microspheres or solid polymeric gel microbeads; solid bioglass or mineral microspheres or granules; solid biological complexes such as DNA and oligonucleotide complexes; living animal or human cells in suspension or adhered to a substrate; liposomes and micelles; etc.

Such gel-forming chitosan compositions can be applied to:

the encapsulation and delivery of therapeutic, pharmaceutical or bioactive agents into a mammalian body, animal or human;

the encapsulation of living, modified or non-modified, animal or human cells for therapeutic purposes;

the delivery of living cells to a specific body's part;

the culture and formation in vitro, of living three-dimensional equivalents of body's tissues or organs for in vivo transplantation purposes or in vitro research or testing studies;

the filling of a defect, formed surgically or through diseases or deficiencies, within a tissue or organ; Ex: bone defect, cartilage defect, etc.

the augmentation of tissues;

the repairing, restoring or regenerating in vivo of body's parts, such as skin, muscles, nerves, tooth including dentin and enamel, bones including alveolar, spongy and cortical bones, cartilages including articular cartilage, arteries, fat pads, meniscus, intervertebral disks, and the like.

the prevention of tissue adhesions;

the action of haemostasis; and any specific pharmaceutical or surgical applications of veterinary or human medicine where a gel-like material may prove to be useful.

The present invention will be more readily understood by referring to the following examples which are given to illustrate the invention rather than to limit its scope.

EXAMPLE 1

Homogenous Acetylation of Chitosan

Figure 1B:
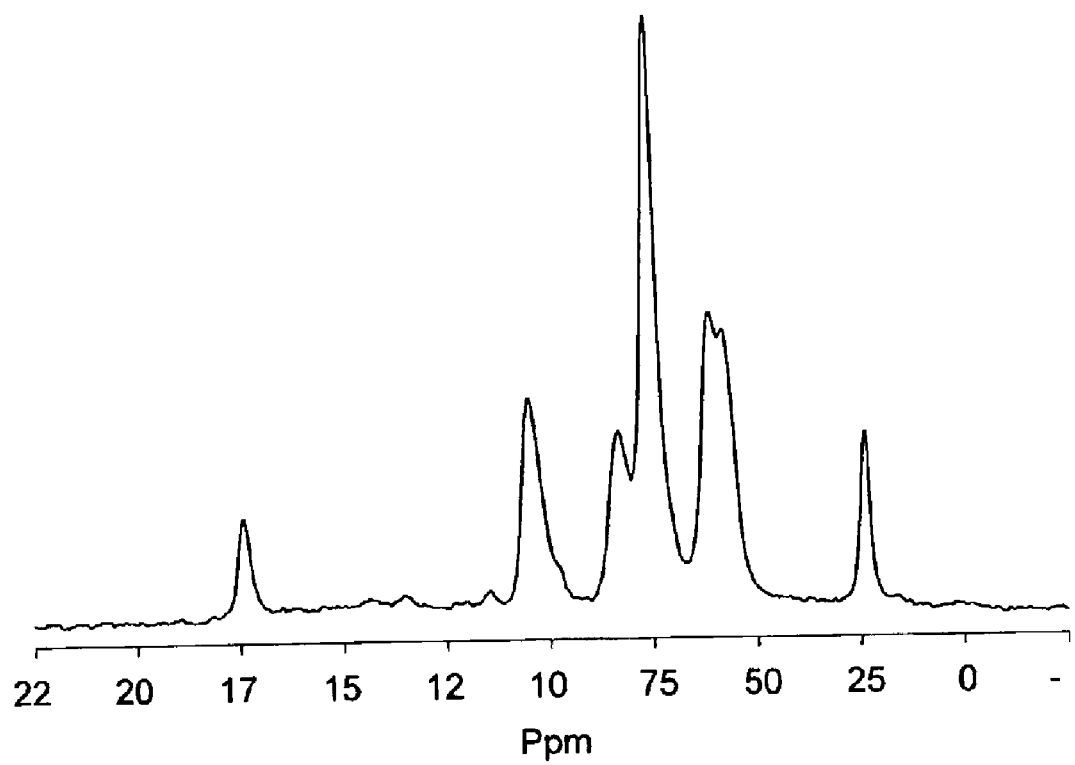
FIG. 1B illustrates a $^{13}C$ NMR spectrum of chitosan reacted with acetic anhydride (AA) at an $AA/NH_2$ ratio of 0.296 and a degree of substitution of 26%.
Figure 1C:
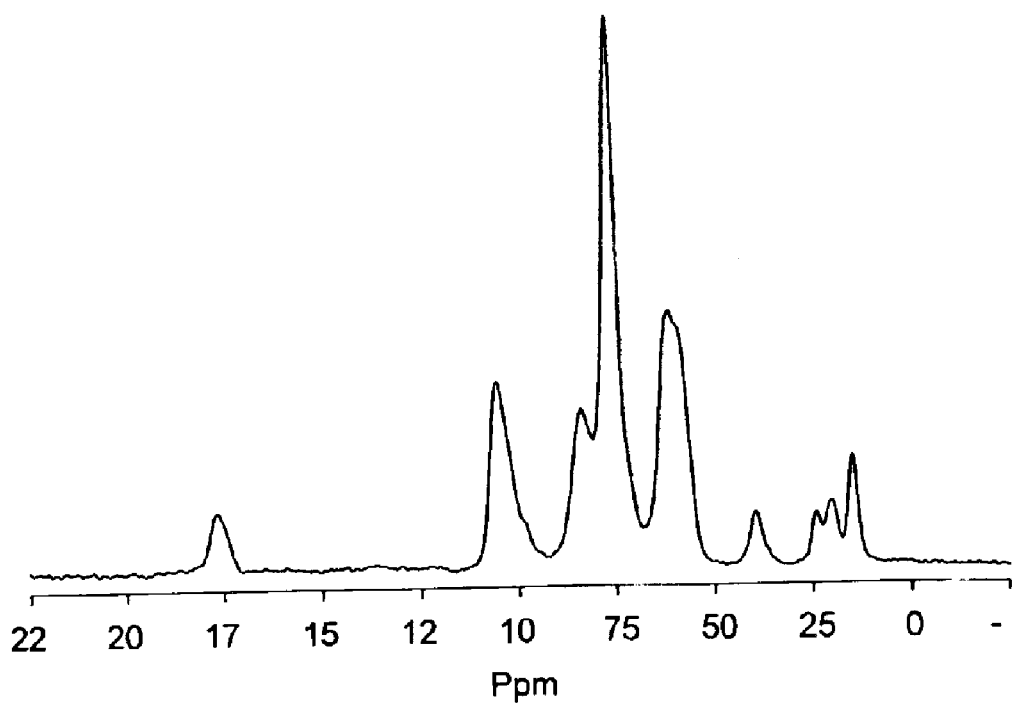
FIG. 1C illustrates a $^{13}C$ NMR spectrum of chitosan reacted with butyric anhydride (BA) at a $BA/NH_2$ ratio of 0.293, with a degree of substitution of 27%.

A chitosan solution (pH~5) was prepared by completely dissolving 1.17 g of chitosan (85% deacetylated) in 50 mL of a solution of HCl (0.1M). The chitosan solution was cooled down to 4° C. and while maintaining the cold temperature, its pH was adjusted to 6.8 by adding ~1.42 g of glycerol-phosphate disodium salt. To the resulting neutral solution, acetic anhydride was added (see Table 1). Then, the reaction was allowed to proceed under continuous stirring and room temperature for about 16 h. At the end, the reaction mixture was transferred into a dialysis bag and dialysed against a large volume of pure water for three days to remove salts and unreacted reagent. The N-acetylated chitosan so obtained was recovered by freeze-drying or by precipitating in 50% water/50% methanol solution of $NH_4OH$ (0.2M), followed by filtration, washing with methanol repeatedly and air-drying. $^{13}C$ NMR analysis confirms the N-acetyl modification (see FIG. 1B) and the integration of peaks allows the determination of a degree of deacetylation close to that obtained by conductimetric titration (see Table 1). FIGS. 1A to 1C are comparative $^{13}C$ NMR spectra of chitosan and modified chitosan. The ratios of integrated peaks at 25 ppm and at 40 ppm with respect to the integrated peaks between 50 and 110 ppm allows the determination of acetyl and butyryl contents respectively.

TABLE I

| Acetic Anhydride (AA) | | % of $NH_2$ substituted | |
|---|---|---|---|
| (g) | AA/$NH_2$ ratio | Titration | $^{13}C$ NMR |
| 0.00 | 0.00 | 0 | 0 |
| 0.1796 | 0.296 | 30 | 26 |
| 0.3592 | 0.592 | 51 | 49 |
| 0.5388 | 0.888 | 67 | 64 |
| 0.8407 | 1.184 | 77 | 72 |

Figure 2A:
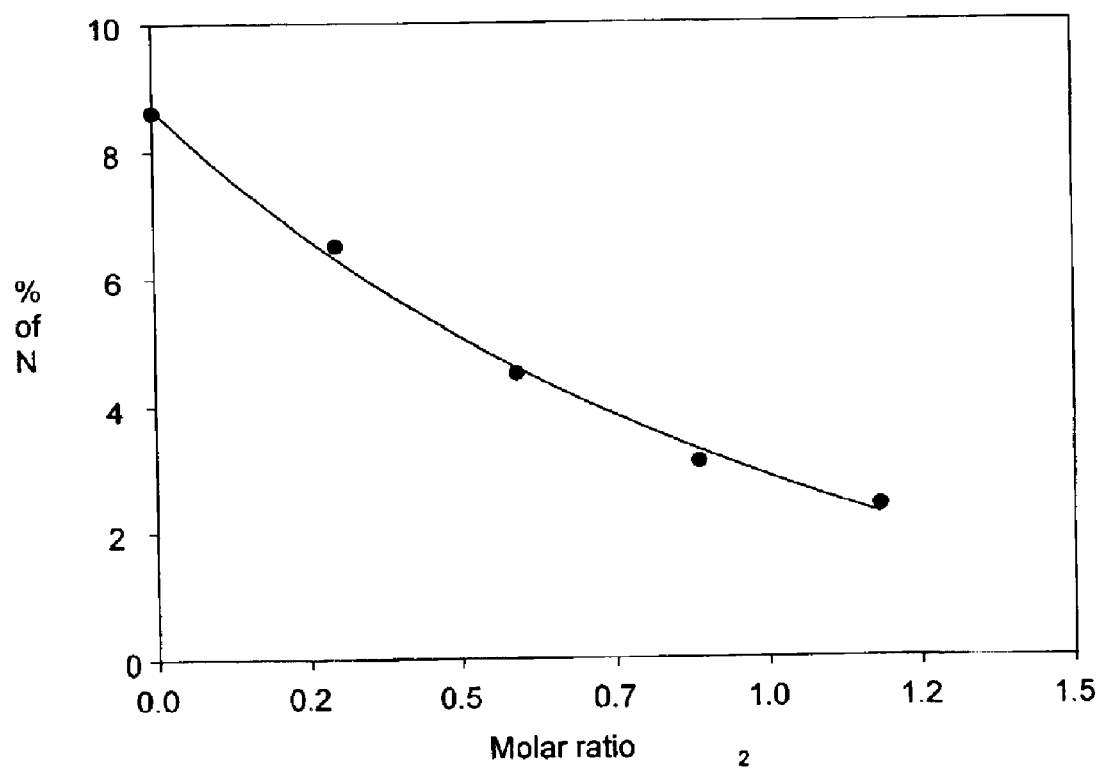
FIGS. 2A and 2B illustrate the glucosamine content after reaction of chitosan with various amounts of acetic anhydride (AA)(FIG. 2A) and with various amounts of butyric anhydride (BA)(FIG. 2B).
Figure 2B:
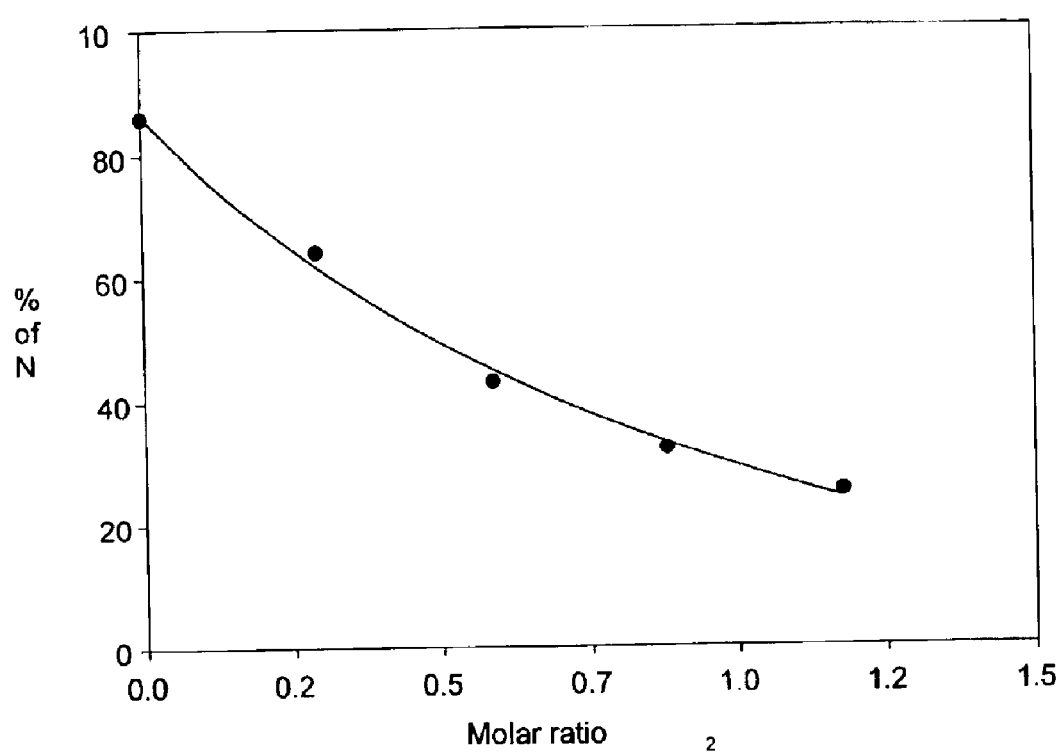

FIG. 2A illustrates the glucosamine content after the reaction of chitosan with various amounts of acetic anhydride.

EXAMPLE 2

Homogenous N-Butyryl Modification of Chitosan

The experiment was performed as in Example 1 above, except that butyric anhydride was used instead acetic anhydride. $^{13}C$ NMR analysis confirms the N-butyryl modification (see FIG. 1C) and the integration of peaks allows the determination of a degree of substitution sensibly close to that deducted from conductimetric titration (see Table 2).

TABLE 2

| Butyric Anhydride (BA) | | % of $NH_2$ substituted | |
|---|---|---|---|
| (g) | BA/$NH_2$ ratio | Titration | $^{13}C$ NMR |
| 0.00 | 0.00 | 0 | 0 |
| 0.2359 | 0.293 | 30 | 27 |
| 0.4729 | 0.588 | 51 | 51 |
| 0.7088 | 0.881 | 66 | 64 |
| 0.9457 | 1.176 | 74 | 72 |

EXAMPLE 3

Chitisan Gel Cross-Linked with Glyoxal 0.47 g of chitosan (85% deacetylated) was entirely dissolved in 20 mL of HCl solution (0.1M). The chitosan solution so obtained had a pH of 5. This solution was cooled down to 4° C. About 0.67 g of glycerol-phosphate disodium salt was added to the chitosan solution to adjust its pH to 6.8. While the resulting solution was maintained at cold temperature, 0.2, 0.1, 0.02 or 0.01 mL of aqueous solution of glyoxal (87.2 mM) was added and homogenised. Transparent gels were formed at 37° C. more or less rapidly depending on the glyoxal concentration (see Table 3).

TABLE 3

| Glyoxal (mM) | Gelation Time at 37° C. (min) |
|---|---|
| 1.744 | immediate |
| 0.872 | immediate |
| 0.262 | 20 |
| 0.174 | 30 |
| 0.087 | 90 |

EXAMPLE 4

Chitisan Gel Cross-Linked with Polyethylene Glycol Diglycidyl Ether

The experiment was performed as in example 3 above, except that glyoxal solution was replaced by polyethylene glycol diglycidyl ether (PEGDGly). Transparent gels were formed at 37° C. more or less rapidly as reported in Table 4, depending on the PEGDGly concentration. The following gelation time were obtained.

TABLE 4

| PEGDGly (mM) | Gelation Time at 37° C. (h) |
|---|---|
| 37.00 | 6 |
| 7.40 | 10 |
| 3.70 | 14 |
| 1.85 | 20 |
| 0.37 | No gelation |

EXAMPLE 5

Preparation of Rapid in situ Gelling Composition by Grafting mPEG on Chitosan in Mild Aqueous Solution for in vivo Administration The present example relates to aqueous compositions containing chitosan and mPEG that rapidly undergo gelation via the formation of covalent and no-covalent linkages between both polymers. The methoxy PEG-succinoyl-N-hydroxysuccinimide ester (mPEG-suc-NHS), and methoxy PEG-carboxymethyl-NHS (mPEG-cm-NHS) were reacted with chitosan under homogeneous conditions in mild aqueous solution to produce hydrogel formulations.

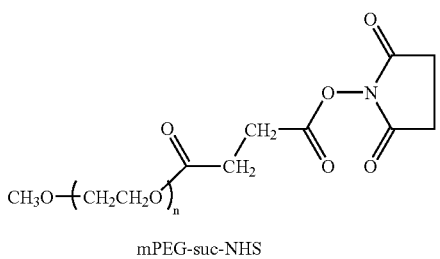

mPEG-suc-NHS

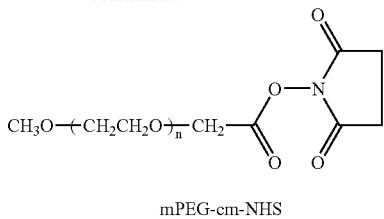

mPEG-cm-NHS

Figure 3:
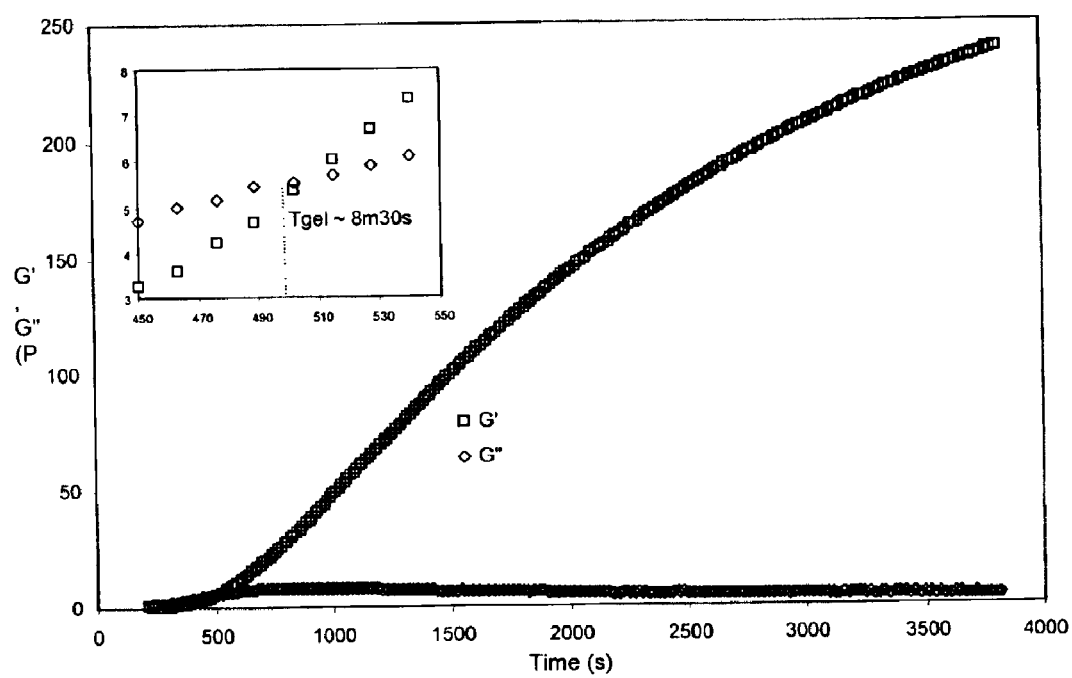
FIG. 3 illustrates the evolution of G' and G" with the time at room temperature for typical formulation comprising [0.20 g of chitosan (90%) dissolved in 9 mL of HCl solution (0.1M), 0.6 g of β-GP dissolved in 1 mL $H_2O$ and 0.05 g of mPEG-suc-NHS dissolved in 10 mL of $H_2O$]

The hydrogel formulations were prepared by dissolving 200 mg of chitosan, (with medium viscosity and a degree of deacetylation of 90%) in 9 mL of HCl solution (0.1 M). The resulting solution was neutralized by adding 600 mg of β-GP dissolved in 1 mL of distilled water. The β-GP buffering solution was carefully added at low temperature (5° C.) to obtain a clear and homogeneous liquid solution. The measured pH value of the final solution was 6.94. To the neutralized chitosan solution, 210 mg of mPEG-suc-NHS (M=5197, 17 g/mol) dissolved in 10 mL of water was added drop wise at room temperature. A transparent and homogeneous mPEG-grafted-chitosan gel was quickly obtained. No precipitate or aggregate was formed during or after the addition. To evidence the gel formation, rheological tests were performed. FIG. 3, representing the evolution of elastic modulus (G') and viscous modulus (G") with the time, for typical formulation, shows a starting increase of G' after about 10 minutes, indicating the incipient gelation. The gelling times of mPEG-grafted-chitosan at R.T. as function of mPEG-suc-NHS concentrations are summarized in Table 5.

TABLE 5

Gelling time at R.T. as function of mPEG-suc-NHS concentration

| mPEG-suc-NHS (mg) | Molar ratio × 100 mPEG-suc-NHS/NH$_2$ | Gelling Time at R.T. (min) |
|---|---|---|
| 210 | 3.71 | 1 |
| 136 | 2.40 | 3 |
| 75 | 1.32 | 6 |
| 50 | 0.88 | 15 |
| 31 | 0.55 | 35 |
| 20 | 0.35 | 90 |

In a similar experiment, replacement of mPEG-suc-NHS by mPEG-cm-NHS led to similar results. Similar results were also obtained when the pH of chitosan solution has been adjusted, to around 6.9, by adding 150 mg of bis-tris (instead of β-GP) dissolved in 1 mL of water. Gelling time also depends on the degree of deacetylation (DDA) and the pH, and no gelation occurred if the pH value is below 6. Without the pH adjustment in the range 6.4 to 7.2, the grafting of mPEG on chitosan cannot occur and therefore the gelation can not take place.

EXAMPLE 6

Modification in situ of Chitosan with mPEG, and Formation of Composite Gels and Self-Hardened Composites A composite gel was prepared from a liquid chitosan aqueous solution (chitosan 2.0% w/v, pH<6) and a solid phase composed of alpha-tricalcium phosphate (1.2 g) and mPEG-suc-NHS (2–7 mg). The mixing of the liquid chitosan solution and solid phase was performed at Liquid/Solid ratio ranging from 0.4 to 0.6 mL/g.

Figure 4A:
FIG. 4A illustrates a chitosan gel obtained by reaction of mPEG-suc-NHS on a chitosan-glycerophosphate aqueous system; the gel has a good strength and can be manipulated without major damages.
Figure 4B:
FIG. 4B illustrates a composite gel prepared from the system described in A) and with solid calcium phosphates; the calcium phosphate loading was 0.45 g/mL; the resulting composite gel retains a remarkable strength and elasticity.

All prepared systems formed strong elastic composite gels (see FIGS. 4A and 4B). When disposed at 37° C. in an aqueous medium, the composite gels progressively turn into solid composite materials, with minimal shrinking. These solids were well-formed after 2 to 7 days. The ultimate compression strengths of such solid composites ranged from 5 to 20 MPa after 4 days.

The modification in situ of chitosan with mPEG combined with the loading in reactive calcium phosphates enables the formation of composite gels and solids.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for chemically-modifying or cross-linking chitosan under homogeneous conditions, said method comprising the steps of:
   a) preparing a clear aqueous solution of chitosan, said solution comprising 0.1 to 10% by weight of a chitosan, and 0.1 to 20% by weight of at least one buffering agent having a pKa between 6.0 and 7.6, said solution having a pH ranging from 6.8 to 7.2; and
   b) dissolving homogeneously at least one reagent into the solution of step a), said reagent reacting with amine groups of chitosan; and said reagent being at a concentration from 0.01 to 10% by weight, chemically modifying or cross-linking said chitosan in the aqueous solution.

2. The method of claim 1 further comprising the step of purifying the chemically-modified or cross-linked chitosan.

3. The method of claim 2, wherein the step of purifying consists of:
   a) dialysing the chemically-modified or cross-linked chitosan;
   b) precipitating the chitosan obtained in step a), with a basic solution;
   c) washing the precipitated chitosan of step b); and
   d) air-drying the washed chitosan of step c).

4. The method of claim 1, wherein said chitosan has a degree of deacetylation between 70% and 100%.

5. The method of claim 1, wherein said buffering agent is a cell culture biological buffer.

6. The method of claim 5, wherein the cell culture biological buffer is selected from the group consisting of phosphate salts, glycerophosphate salts, N,N-Bis(2-hydroxyethyl)-2-aminoethanesulfonic acid (BES); N,N-Bis(2-hydroxyethyl)-3-amino-2-hydroxypropanesulfonic acid (DIPSO); N-(2-Hydroxyethyl)piperazine-N'-(4-butanesulfonic acid) (HEPBS); 4-(2-Hydroxyethyl)piperazine-1-ethanesulfonic acid (HEPES); 2-Morpholinoethanesulfonic acid (MES); 4-(N-Morpholino)butanesulfonic acid (MOBS); 4-Morpholinepropanesulfonic acid (MOPS); β-Hydroxy-4-morpholinepropanesulfonic acid (MOPSO); 2-Bis(2-hydroxyethyl)amino-2-(hydroxymethyl)-1,3-propanediol (BIS-TRIS); and 1,3-Bis[tris(hydroxymethyl)methylamino] propane (BIS-TRIS propane), or a mixture thereof.

7. The method of claim 1, wherein said reagent is selected from the group consisting of aldehydes, anhydride acids, azides, azolides, carboimides, epoxides, esters, glycidyl ethers, halides, imidazoles, imidates, succinimides, succinimidyl esters, acrylates and methacrylates, or a mixture thereof.

8. The method of claim 1, wherein said reagent is water-soluble and has at least two reactive groups selected from the group consisting of aldehydes, azides, azolides, esters, glycidyl ethers, halides, imidazoles, imidates, succinimides, succinimidyl esters, acrylates and methacrylates, or a combination thereof.

9. The method of claim 1, wherein said reagent is poly(ethylene glycol) di-glycidyl ether, poly(ethylene glycol) di-tresylate, poly(ethylene glycol) di-isocyanate, poly(ethylene glycol) di-succinimidyl succinate, poly(ethylene glycol) di-succinimidyl propionate, di-succinimidylester of carboxymethylated poly(ethylene glycol), poly(ethylene glycol) di-benzotriazole carbone, carbonyldimidazole di-functiona-lized poly(ethylene glycol), or poly(ethylene glycol) di-nitrophenyl carbonate.

10. The method of claim 1, wherein said reagent is a di-functionalized water-soluble polymer selected from the group consisting of poly(alkylene glycol), poly(alkylene oxide), poly(vinyl alcohol) and poly(vinyl pyrrolidone).

11. The method of claim 1, wherein said reagent is glutaraldehyde, formaldehyde, glyoxal, or a dialdehyde reagent.

12. The method of claim 1, wherein said reagent has an ester reactive group selected from the group consisting of bi-functional succinimidyl, sulfo-succinimidyl, N-hydrosuccinimidyl and N-sulfo-succinimidyl ester group.

13. The method of claim 1, wherein said reagent has an imidoester reactive group selected from the group consisting of di-methylpimelimidate, di-methyladipimidate, di-methylsuberimidate, and di-methylpropionimidate reactive group.

14. The method of claim 1, wherein said reagent has a phenylazide, hydrazide, hydroxyphenyl azide or nitrophenyl azide group.

15. The method of claim 1, wherein the reagent is an acid anhydride.

16. The method of claim 15, wherein the acid anhydride is selected from the group consisting of acetic anhydride, propionic anhydride and butyric anhydride.

17. The method of claim 1, wherein the solution of step a) further comprises a pharmaceutical agent, a therapeutic agent or a bioactive agent.

18. The method of claim 1, wherein the solution of step a) comprises suspended cells.

19. The method of claim 18, wherein the suspended cells are suspended living mammalian cells.

20. A method of preparation of a chitosan based aqueous gel composition which comprises the steps of:
    a) preparing a water-based solution component comprising 0.1 to 10% by: weight of chitosan, having a degree of deacetylation between 70% and 100%, and 0.1 to 20% by weight of a glycerophosphate salt; said solution having a pH in the range between 6.4 and 7.2;
    b) preparing a solid component comprising at least a water-soluble methoxy-poly(ethylene glycol) reagent, having a molecular weight between 2,000 and 10,000, said reagent being functionalized with a chemical group reactive with free amine; and
    c) mixing homogeneously said solution component and said solid component to form a uniform and homogeneous solution, having 0.01 to 10% by weight of the methoxy-poly(ethylene glycol) reagent, wherein a homogeneous N-modification or N-grafting of chitosan chains and the formation of a homogeneous uniform aqueous gel occurs.

21. The method of claim 20, wherein said reagent is selected in a group consisting of methoxy PEG-succinoyl-N-hydroxysuccinimide ester (mPEG-suc-NHS) and methoxy PEG-carboxymethyl-NHS (mPEG-cm-NHS).

22. The method of claim 20, wherein said composition is liquid prior to said formation of a homogeneous uniform aqueous gel.

23. The method of claim 1, further comprising the steps of:
    c) adding a material of biological origin,
wherein said material of biological origin is selected from the group consisting of autograft, allograft xenograft, crushed bone, demineralized bone powder, solid animal proteins, human proteins, animal living cells and human living cells.

* * * * *